United States Patent [19]
Moss

[11] Patent Number: 5,871,780
[45] Date of Patent: Feb. 16, 1999

[54] PEST-CONTROLLING COMPOSITION

[75] Inventor: James Iredell Moss, Gainesville, Fla.

[73] Assignee: J. T. Easton & Co., Inc., Twinsburgh, Ohio

[21] Appl. No.: 906,072

[22] Filed: Aug. 5, 1997

Related U.S. Application Data

[62] Division of Ser. No. 536,469, Sep. 19, 1995, Pat. No. 5,667,816.

[51] Int. Cl.$^6$ .......................... A01N 43/90; A01N 43/42; A01N 59/14
[52] U.S. Cl. .......................... 424/659; 424/660; 514/263; 514/264; 514/307
[58] Field of Search .................................. 424/659, 660; 514/263, 264, 307

[56] References Cited

U.S. PATENT DOCUMENTS

| | | | |
|---|---|---|---|
| 2,524,738 | 10/1950 | Snell et al. | 167/58 |
| 2,968,590 | 1/1961 | Polquin | 167/14 |
| 4,299,258 | 11/1981 | Brite | 141/1 |
| 4,438,090 | 3/1984 | Brite | 424/7.1 |
| 4,461,758 | 7/1984 | Brite | 424/10 |
| 4,759,930 | 7/1988 | Granirer et al. | 424/148 |
| 4,783,457 | 11/1988 | Nathanson | 514/227.2 |
| 4,883,801 | 11/1989 | Nathanson | 514/263 |
| 4,892,871 | 1/1990 | Nathanson | 514/227.2 |
| 4,902,690 | 2/1990 | Nathanson | 514/213 |
| 4,944,950 | 7/1990 | Sakharova | 424/623 |
| 4,959,221 | 9/1990 | Holmes | 424/659 |
| 4,988,516 | 1/1991 | Herring | 424/659 |
| 4,996,053 | 2/1991 | Hatcher | 424/410 |
| 5,223,270 | 6/1993 | Jones | 424/659 |
| 5,273,761 | 12/1993 | Kim et al. | 424/659 |
| 5,346,700 | 9/1994 | Stapleton et al. | 424/410 |
| 5,384,120 | 1/1995 | Blum | 424/84 |

OTHER PUBLICATIONS

Article entitled *Oral Toxicity of Boric Acid and Other Boron Compounds to Immature Cat Fleas (Siphonaptera: Pulicidae)* by John H. Klotz et al. 1994 pp. 1534–1536.

Article entitled Renewed Interest in an Ancient Compound by John Klotz & Jim Moss, *Pest Control Technology*, Nov. 1994 issue, pp. 55–58.

The Merck Index, 11th Ed. (1989) p. 1111.

*Primary Examiner*—Allen J. Robinson
*Attorney, Agent, or Firm*—D. Peter Hochberg

[57] ABSTRACT

A pest-controlling composition comprised of a borate compound and a compound resulting in elevated concentrations of cyclic AMP, such as a phosphodiesterase enzyme (PDE) inhibitor, or a formamidine. The borate compound of the pest-controlling composition has increased toxicity as compared to a borate compound acting alone.

7 Claims, No Drawings

PEST-CONTROLLING COMPOSITION

This is a divisional of application Ser. No. 08/536,469 filed on Sep. 19, 1995 now U.S. Pat. No. 5,667,816.

FIELD OF THE INVENTION

The present invention relates generally to a pest-controlling composition, and more particularly, to a pest-controlling composition comprised of a borate compound and a compound resulting in elevated concentrations of 3'-5'-cyclic adenosine monophosphate (cAMP).

BACKGROUND OF THE INVENTION

Compositions containing boron have long been used in the field of pest control, particularly in insecticides. More recently, boron compounds have declined in use due to the availability of modern synthetic insecticides. However, there are several drawbacks associated with synthetic insecticides, including resistance development in the pests, re-registration costs, and safety concerns by homeowners. These problems have renewed interest in boron compounds for use in pest control.

Historically, the use of boron compounds in structural pest control has been directed at cockroaches. More recently, research and development has been aimed at the use of boron compounds (e.g., boric acid) in the control of ants, cockroaches, fleas, and wood-destroying organisms.

Among the pests most sought to be controlled are ants, cockroaches and fleas. With ants, if a bait is sufficiently attractive it will be rapidly carried back to the ant nest and distributed to the entire ant colony. To effectively kill the ant colony, a slow-acting toxicant is required so that the ants have sufficient time to collect and distribute the insecticide before it reaches a lethal level.

In low concentrations, boric acid acts as a slow-acting toxicant. One advantage to using boric acid to kill ants is its solubility in water. Not only is water a convenient carrier, but it also helps meet the ants' need for moisture in their diet. Additionally, liquid baits exploit the natural feeding habits of sweet-eating ants that collect honeydew, nectar and other plant juices. Another advantage of using boric acid to kill ants is that it acts like a desiccant (i.e., a substance that removes moisture), causing dehydration of the ants, which causes them to consume more of the liquid bait.

With respect to control of cockroaches, boric acid has been used primarily as a stomach poison, either as a dust that is ingested by the cockroach during grooming, or as a toxicant incorporated into a bait. Only secondarily does the boric acid kill by contact. Traditionally, the concentration of boric acid used in cockroach bait has been very high. In some cases, the bait may consist of 50% or more boric acid.

Boric acid is also useful in the control of fleas. In this regard, it has been found that boric acid effectively controls fleas when applied to the actively feeding larval stages of the fleas. Killing of the larvae breaks the life cycle of the fleas, and leads to eventual control of the flea population. The boric acid is believed to kill through ingestion since boric acid appears to lack contact toxicity in fleas.

Among the problems encountered with the use of borates (e.g., boric acid or triethyl borate) as a pest-controlling composition is that borates are relatively slow acting and lack potency. Accordingly, prior art pest-controlling compositions use high concentrations of borates. However, the use of increased borate concentrations has numerous drawbacks. In this regard, there is a potential for bait avoidance by the pests. For instance, fire ants are known to avoid ant baits having a borate content of 1% or more. Furthermore, high borate concentrations also pose a hazard to the environment. In this respect, borates are toxic or injurious to plants (i.e., phytotoxic). Moreover, the increased borate concentrations may also threaten customer safety. The prior art fails to provide a pest-controlling composition using borate compounds in low concentrations, and which also provides quick and effective pest control.

The present invention overcomes these and other drawbacks of using borate compounds in a pest-controlling composition.

SUMMARY OF THE INVENTION

According to the present invention, there is provided a pest-controlling composition comprising a borate compound containing oxygen and a compound resulting in elevated concentrations of 3'-5'-cyclic adenosine monophosphate (cAMP).

It is an object of the present invention to provide a pest-controlling composition that increases the toxicity of borate compounds, thus allowing the use of lower borate compound concentrations in the pest-controlling composition and still yielding fast and effective pest control.

It is another object of the present invention to provide a pest-controlling composition having an increased toxicity of borate compounds over the toxicity of borate compounds used alone at the same concentration.

It is still another object of the present invention to provide a pest-controlling composition including a borate compound having an increased toxicity at a lower concentration of borate compound.

Another object of the present invention is to provide a pest-controlling composition having a borate compound, which reduces or eliminates bait avoidance.

These and other objects will become apparent from the following description of a preferred embodiment taken together with the accompanying drawings and the appended claims.

DETAILED DESCRIPTION OF THE PREFERRED EMBODIMENT

The present invention will be described below with reference to test results for insecticidal bait compositions for controlling cockroaches. However, it should be appreciated that it is contemplated that the present invention is effective for controlling other insect pests, such as ants (e.g., carpenter, fire, ghost, pyramid, pharaoh, crazy and "pavement" ants), fleas, ticks, and the like, as well as non-insect pests (e.g., rodents).

3'-5'-cyclic adenosine monophosphate (hereinafter referred to as "cAMP" or "cyclic AMP") is a nucleotide found in almost all animal tissues (vertebrate and invertebrate) and in bacteria. Cyclic AMP is composed of phosphate, ribose sugar and adenine. It is synthesized from ATP (adenosine triphosphate) in living cells by a reaction catalyzed by an enzyme called adenylate cyclase, which appears to be built into the cell membrane. It has been discovered that substances that prevent the breakdown of cAMP, and substances which increase the production of cAMP will increase the toxicity of borate compounds to the pest, as compared to the toxicity of borate compounds used alone.

Many, if not all cells of plants, animals, and microbes (except viruses), have a "second messenger" system which allow the cells to take some external signal or message and convert that signal into some sort of response by the cell. One such "second messenger" system generates cAMP as a "second messenger." An extracellular "first messenger" goes to a target cell and there stimulates production of an intracellular "second messenger" which is cAMP. More specifically, the binding of the "first messenger" to a highly specific receptor site on the outer surface of the target cell activates the enzyme adenylate cyclase, which catalyzes production of more cAMP on the inner surface of the cell membrane. The increased amounts of cAMP then initiate the cell's characteristic responses to the "first messenger." In particular, the increased amounts of cAMP interact with cytoplasmic enzyme systems. In this regard, cAMP actuates a protein kinase enzyme, which in turn activates certain enzymes and inactivates others by phosphorylating them. In summary, the initial extracellular signal (the "first messenger") is converted into an intracellular signal (cAMP, or "second messenger") that the chemical machinery of the cell can more readily understand.

There are several signals (i.e., "first messengers") which will cause adenylate cyclase to produce cAMP, depending on the purpose of the cell. For instance, cells which respond to the neurochemical octopamine ("first messenger") do so by having receptor sites for octopamine on the outer surface of the cell. When octopamine binds to this external receptor, the receptor (i.e., a protein which spans the cell membrane) causes the internal enzyme, adenylate cyclase, to produce cAMP. While cAMP production is linked to octopamine in octopamine-sensitive cells, this "second messenger" system for producing cAMP is not unique to octopamine-sensitive cells. In this respect, borate compounds are understood to cause adenylate cyclase to produce cAMP, to prevent cAMP breakdown, or to exacerbate the effects of elevated cAMP, in cells which are not sensitive to octopamine. Accordingly, borate compounds are not dependent on octopamine-sensitive cells for effectiveness.

To prevent excessive responses by cells, the cells also contain phosphodiesterase enzymes (PDE) which break down cAMP. An excess of cAMP will be produced if the action of the PDE are blocked. Examples of substances which inhibit the production of PDE include methylxanthines (such as caffeine and theophylline), papaverine, and other compounds.

It will also be appreciated that there are also substances which will increase the production of cAMP, either directly or indirectly. For example, formamidines, such as chlordimeform (CDM) and Amitraz, increase the production of cAMP. These compounds elevate cAMP production via octopamine agonist action.

Substances which inhibit the breakdown of cAMP (i.e., PDE inhibitors) and substances which increase the production of cAMP (e.g., formamidines), will increase the toxicity to pests of borate compounds over the toxicity of the borate compounds used alone. The inverse is also true, in that borate compounds will increase the toxicity of substances which inhibit PDE production and substances which elevate cAMP.

The combination of borate compounds and PDE inhibitors (or substances which increase cAMP production) results in the correlated action of both compounds which, together, have greater total effect than the sum of their individual effects. Accordingly, a synergistic effect is obtained when using a borate compound with a PDE inhibitor or a compound which increases cAMP production.

It should be understood that the term "borate compounds" is used herein to refer to any trivalent borate compound containing oxygen attached to boron.

As will be discussed below, mixtures of borate compounds with PDE inhibitors, or substances which increase cAMP production, will shorten the "time to death" of the pests (e.g., cockroaches) over the "time to death" of the borate compounds used alone. Use of a PDE inhibitor or a substance increasing cAMP production will increase the action and potency of the borate compounds by increasing their toxicity. Accordingly, the time needed to kill the targeted pests with the combined substances will be reduced relative to the time needed to kill the targeted pests with the borate compound alone. Due to the increased toxicity of the borate compounds when used with a PDE inhibitor or a substance increasing cAMP production, the concentrations of borate compounds can be lowered in a pest-controlling composition, while still maintaining the composition's speed and effectiveness.

Several benefits are obtained by lowering the borate compound concentration needed to control the pests. Among these benefits are reduction or elimination of bait avoidance, which is a particular problem with respect to fire ants, which typically avoid ant bait having a concentration of 1% or more of borate compounds. Moreover, the phytotoxicity of the pest-controlling composition is reduced, thus minimizing environmental problems. In addition, consumer safety is enhanced by a reduction in the borate compound concentration.

According to a preferred embodiment of the present invention, the pest-controlling composition is comprised of a borate compound and a compound resulting in an elevated concentration of cAMP. For instance, the borate compound may be boric acid or triethyl borate. The compound resulting in elevated concentrations of cAMP may be a PDE inhibitor or a formamidine. For instance, the PDE inhibitor may be a methlxanthine (such as caffeine, theophylline, or dibutyrl cyclic AMP) or papaverine. Examples of suitable formamidines include chlordimeform (CDM) and Amitraz.

In a preferred embodiment of the invention, the pest-controlling composition is comprised of boric acid and caffeine. Caffeine is a preferred PDE inhibitor because it is already a government approved food additive, is relatively inexpensive, and is readily available. Caffeine is the least likely of the PDE inhibitors to cause regulatory problems. In this regard, caffeine is used in numerous foods, used in several drug formulations, and sold over the counter as an appetite suppressant and sleep suppressant. As to cost, reagent grade caffeine costs approximately $41.00 per kilogram, or approximately $16.00 per kilogram in wholesale bulk. These costs compare very favorably to the costs associated with other PDE inhibitors.

Papaverine is a "natural product" found in opium. In the past, it has been synthesized and used as a smooth muscle relaxant. However, while papaverine is an excellent borate synergist, it is more costly than caffeine and may pose greater government regulatory problems than caffeine.

It should be appreciated that the pest-controlling composition according to the present invention may include a borate compound with both a PDE inhibitor and a formamidine (such as CDM). As discussed above, a PDE inhibitor prevents the breakdown of cAMP, while formamidines increase cAMP production. These compounds will therefore act synergistically when used with a borate compound. In this respect, the killing power of combined use of the borate compound and either a PDE inhibitor or formamidine is much greater than the sum of the killing power of the borate compound and the PDE inhibitor or formamidine used separately. Moreover, this embodiment of the invention provides a pest-controlling composition which will effect cells with octopamine receptors, as well as cells without octopamine receptors.

Tables I–IV set forth below provide a series of test results conducted on adult male German cockroaches. It should be noted that all mortality test results were corrected using Abbott's formula in accordance with standard toxicological practice. The "toxin" is the primary compound for killing the roaches, while the "synergist" is the compound that causes a synergistic effect. However, as will be seen from the test results, the toxin also acts as a synergist. Accordingly, the toxin and the synergist are actually "co-synergists."

TABLE I

| Test No. | Toxin | Bait Form | Percentage | Synergist | Bait Form | Percentage | Lethal Time (in hours) For 50% Kill (LT-50) | Synergism Ratio |
|---|---|---|---|---|---|---|---|---|
| 1 | boric acid | liquid | 0.19 | — | — | — | 191 | 1 |
|  | boric acid | liquid | 0.19 | caffeine | liquid | 0.97 | 120 | 1.59 |
| 2 | boric acid | liquid | 0.31 | — | — | — | 125 | 1 |
|  | boric acid | liquid | 0.31 | caffeine | solid | 2 | 80 | 1.56 |
|  | caffeine | solid | 2.00 | — | — | — | 367 | — |
| 3 | boric acid | liquid | 0.62 | — | — | — | 74 | 1 |
|  | boric acid | liquid | 0.62 | caffeine | solid | 0.8 | 61 | 1.21 |
|  | boric acid | liquid | 0.62 | caffeine | solid | 2 | 45 | 1.66 |
|  | caffeine | solid | 2.00 | — | — | — | 367 | — |
| 4 | boric acid | solid | 0.10 | — | — | — | no kill | — |
|  | boric acid | solid | 0.10 | caffeine | solid | 2 | 268 | — |
|  | boric acid | solid | 0.10 | papaverine | liquid | 1 | 82 | — |
|  | papaverine | liquid | 1.00 | — | — | — | 193 | — |
|  | caffeine | solid | 2.00 | — | — | — | 367 | — |
| 5 | boric acid | solid | 0.20 | — | — | — | no kill | — |
|  | boric acid | solid | 0.20 | caffeine | solid | 2 | 172 | — |
|  | boric acid | solid | 0.20 | papaverine | liquid | 1 | 95 | — |
|  | papaverine | liquid | 1.00 | — | — | — | 193 | — |
|  | caffeine | solid | 2.00 | — | — | — | 367 | — |
| 6 | boric acid | solid | 0.40 | — | — | — | no kill | — |
|  | boric acid | solid | 0.40 | caffeine | solid | 1 | 502 | — |
|  | boric acid | solid | 0.40 | caffeine | solid | 2 | 293 | — |
|  | boric acid | solid | 0.40 | papaverine | liquid | 1 | 71 | — |
|  | papaverine | liquid | 1.00 | — | — | — | 193 | — |
|  | caffeine | solid | 2.00 | — | — | — | 367 | — |
| 7 | boric acid | solid | 1.00 | — | — | — | 335 | 1 |
|  | boric acid | solid | 1.00 | caffeine | solid | 1 | 191 | 1.75 |
|  | boric acid | solid | 1.00 | caffeine | solid | 2 | 123 | 2.73 |
|  | boric acid | solid | 1.00 | papaverine | liquid | 1 | 89 | 3.77 |
|  | papaverine | liquid | 1.00 | — | — | — | 193 | — |
|  | caffeine | solid | 2.00 | — | — | — | 367 | — |
| 8 | boric acid | solid | 3.00 | — | — | — | 87 | 1 |
|  | boric acid | solid | 3.00 | papaverine | liquid | 1 | 56 | 1.56 |
|  | papaverine | liquid | 1.00 | — | — | — | 193 | — |
| 9 | boric acid | solid | 6.00 | — | — | — | 115 | 1 |
|  | boric acid | solid | 6.00 | papaverine | liquid | 1 | 64 | 1.80 |
|  | papaverine | liquid | 1.00 | — | — | — | 193 | — |
| 10 | boric acid | solid |  | — | — | — | 91 | 1 |
|  | boric acid | solid | 8.00 | caffeine | solid | 8 | 46 | 1.98 |
|  | caffeine | solid | 8.00 | — | — | — | 166 | — |

TABLE II

| Hours Dosed | Toxin | Bait Form | Lethal Dose (in percentage) for 50% Kill (LD-50) | Synergist | Bait Form | Percentage | Synergism Ratio |
|---|---|---|---|---|---|---|---|
| 144 | boric acid | solid | 4.25 | — | — | — | 1 |
| 144 | boric acid | solid | 2.19 | caffeine | solid | 1 | 1.94 |
| 144 | caffeine | solid | 5.98 | — | — | — | — |

TABLE III

| Hours Dosed | Toxin | Form | Mass (in micrograms per gram of roach) for 50% Kill (LD-50) | Hours Pretreated with Synergist | Synergist | Bait Form | Percentage | Synergism Ratio |
|---|---|---|---|---|---|---|---|---|
| 48 | CDM | topical | 34.7 | — | — | — | — | 1 |
| 48 | CDM | topical | 12.7 | 4 | boric acid | liquid | 0.62 | 2.72 |
| 48 | CDM | topical | 9.18 | 24 | boric acid | liquid | 0.31 | 3.78 |
| 48 | CDM | topical | 9.53 | 48 | boric acid | liquid | 0.19 | 3.64 |

TABLE IV

| Hours Dosed | Toxin | Form | Mass (in micrograms per gram of roach) for 50% Kill (LD-50) | Synergist | Form | Mass (in microgram per gram of Roach) | Synergism Ratio |
|---|---|---|---|---|---|---|---|
| 48 | triethyl borate | topical | 526 | — | — | — | 1 |
| 48 | triethyl borate | topical | 166 | Amitraz | topical | 10 | 3.16 |

Referring now to Table I, it should be noted that where the "bait form" is indicated as "liquid," the respective compound (i.e., the toxin or synergist) has been mixed with water. Furthermore, the respective percentage refers to the weight of the compound per the total volume of the liquid bait. Similarly, where the "bait form" is indicated as "solid," the respective compound (i.e., the toxin or synergist) has been wet mixed with rat chow and then dried. Furthermore, the respective percentage refers to the weight of the compound per the total weight of the solid bait. It will be appreciated that where the toxin compound is provided in bait form different from the bait form of the synergist compound, the toxin compound and synergist compound were provided to the roaches by a different bait source.

The term "LT-50" refers to the number of hours required to kill one-half (i.e., 50%) of the roaches. The synergism ratio shown in the last column is provided to indicate improvements in killing power when a synergist is used. The synergism ratio is "1" for the toxin used effectively alone without a synergist. Subsequent synergism ratios are computed by dividing the LT-50 for the toxin used alone by the LT-50 for the toxin used with a synergist. A synergism ratio of "2" would indicate that a toxin used in combination with the synergist is twice as potent (or reduced the time to kill by one-half) than the toxin used alone. It should be noted that a synergism ratio cannot be computed when the toxin used alone is ineffective (i.e., there is "no kill"). In this regard, the term "no kill" means that no cockroaches were killed during the testing period of over four weeks.

It can be seen from the tests shown in Table I that when caffeine or papaverine is used as a synergist in combination with boric acid, the lethal time for killing 50% of the roaches (LT-50) is significantly lower than the LT-50 for boric acid used alone at the same concentration or "percentage." Accordingly, lower concentrations of boric acid can be used, while obtaining improved LT-50 results. For instance, in Test No. 6, when boric acid is used alone as a toxin at a percentage of 0.40%, no roaches are killed. In contrast, when the boric acid is used at the same concentration (i.e., 0.40%) with a caffeine synergist at 1%, the LT-50 is 502 hours. When boric acid is again used at the same concentration (i.e., 0.40%) with a caffeine synergist at 2%, the LT-50 drops to 293 hours. Moreover, when the boric acid is once again used at a concentration of 0.40% with a papaverine synergist at 1%, the LT-50 drops further to 71 hours.

Table I also illustrates that when caffeine or papaverine is used as a synergist in combination with boric acid, the LT-50 is significantly lower than the LT-50 for caffeine or papaverine used alone as the toxin in the same percentage concentration. For instance, in Test No. 4, when boric acid is used as a toxin at 0.10%, with a caffeine synergist at 2%, the LT-50 is 268 hours. In contrast, when caffeine is used alone as a toxin at 2%, the LT-50 rises to 367 hours. Thus, the boric acid synergizes the caffeine and papaverine.

Table II provides test results for a fixed number of hours in which the roaches are exposed to the bait. In this respect, mortality is assessed 144 hours after dosing. The lethal dose for killing 50% of the roaches (LD-50) is determined for boric acid acting alone as a toxin, boric acid acting as a toxin with a caffeine synergist, and caffeine acting alone as a toxin. As can be seen from Table II, when boric acid acts alone, it must be used in a higher concentration to kill 50% of the roaches in a 144-hour dosing period, than when boric acid is used with a caffeine synergist. Similarly, when caffeine acts alone, it must be used in a higher concentration to kill 50% of the roaches in a 144-hour dosing period, than when caffeine is used as a synergist with boric acid.

It should be noted that for each test in Table II the bait form is a solid. Accordingly, the compounds have been wet mixed with rat chow, then dried, and the percentages for the toxin and synergist refer to the weight of the toxin or synergist per the total weight of the solid bait.

Table III illustrates the effects of using boric acid with a formamidine. In the test shown, the formamidine is chlordimeform (CDM). However, it will be appreciated that other formamidines, such as Amitraz, are also suitable.

It should be understood that a "topical" form for the toxin means that the toxin is dissolved in acetone and then topically applied to the roaches (i.e., there is no bait). The mass of the toxin for the LD-50 is the mass of the toxin only (i.e., does not include the acetone). Since the synergist bait form is a liquid, the synergist has been added to water, and the percentage of the synergist refers to the weight of the synergist per the total volume of the liquid bait. Furthermore, it should be understood that in the test shown in Table III, the roaches were pretreated with the synergist before they were given the toxin. The number of pretreatment hours is indicated. The column labeled "Hours Dosed w/Toxin" refers to the number of hours the roaches were dosed with the toxin after pretreatment with the synergist.

Table III shows that the mass of CDM needed to kill 50% of the roaches when using CDM alone is much greater than the mass of CDM needed to kill 50% of the roaches when using CDM with a boric acid synergist.

Turning now to Table IV, this table is included to show how a borate compound other than boric acid (i.e., triethyl borate), and a formamidine synergist (i.e., Amitraz) are also effective in controlling pests. As in Table III, the toxin is applied topically by dissolving the toxin in acetone and topically applying it to the roaches (i.e., there is no bait). Likewise, the synergist is applied topically. The mass values for the toxin and synergist do not include the mass of the acetone. The toxin, triethyl borate, is applied topically because triethyl borate penetrates the roaches' cuticle and is believed to be broken down internally by the roach to boric acid.

Table IV illustrates that the mass of triethyl borate needed to kill 50% of the roaches (LD-50), in 48 hours, is significantly greater than the mass of triethyl borate needed to kill 50% of the roaches (LD-50), in 48 hours, when used with Amitraz. The synergism ratio indicates that use of the Amitraz synergist makes the pest-controlling composition over three times more potent, while using a reduced amount of triethyl borate.

In view of the foregoing test results illustrated in Tables I–IV, a preferred pest-controlling composition for cockroaches and ants in the form of a liquid bait comprises approximately 0.1% to 1% boric acid and approximately 0.5% to 2% caffeine. The foregoing percentages refer to the weight of the compound per the total volume of the liquid bait.

More specifically, a preferred pest-controlling composition in liquid form for cockroaches or ants is 0.5% boric acid and 1% caffeine. It should be noted that there may be some repellency with fire ants at 0.5% boric acid, therefore, for ants, the boric acid may be lowered to between approximately 0.2% and 0.3%. Moreover, it should be understood that cockroaches may avoid percentages of caffeine that exceed much over 1%.

The preferred pest-controlling composition for cockroaches and ants in the form of a solid bait comprises approximately 0.1% to 10% boric acid and approximately 0.5% to 2% caffeine. The foregoing percentages refer to the weight of the compound per the total weight of the solid bait.

For a preferred pest-controlling composition in solid form for cockroaches the composition preferably comprises 1.0% boric acid and 1.0% caffeine. For ants, the preferred concentrations are 0.2% boric acid and 1.0% caffeine. The lower boric acid concentration for ants provides a slow kill, which is more effective in wiping out the entire colony. This contrasts with roach control where a fast kill is desirable to quickly eliminate the cockroaches.

While it is understood that liquid baits may include water and solid baits may include a dry bait food (such as distillers grain or rat chow), the baits may also include an attractant such as sucrose, a preservative, pH controllers, an anti-oxidant and a mold inhibitor.

A preservative may be added to help preserve the toxin and synergist. With regard to pH controllers, it may be desirable to fix the pH level to maintain quality control. In this respect, the pH level may affect the action of the preservative, the action of the toxin and synergist, the shelf-life of the composition and the taste of the composition. It should be noted that a borate compound, such as boric acid, will probably lower the pH level, while a PDE inhibitor, such as caffeine, will probably raise the pH level. A preferred pH level is approximately 6.5. Hydrochloric acid and sodium hydroxide are examples of suitable pH controllers. An anti-oxidant may be added to keep the PDE inhibitor (i.e., caffeine) from breaking down through oxidation. The mold inhibitor is desirable to prevent the formation of mold during storage and use of the pest-controlling composition.

While a range of percentages has been provided above for a pest-controlling composition suitable for controlling both ants and cockroaches, it should be understood that for controlling ants, the lower end of the boric acid range will likely be preferred. In this regard, some species of ants (e.g., fire ants) may avoid high boric acid concentration. Moreover, in controlling ants it is desirable to have a slow kill, so that the ants have an opportunity to feed the bait to the whole colony, including the queen.

While the data set forth in Tables I–IV is for cockroaches, the results will be similar for ants. In this respect, caffeine should have, by all conventional scientific understanding, the same effect on ants as it has on cockroaches. In fact, as a group, ants are less able to detoxify chemicals. Therefore, the caffeine should be at least as effective on ants as on the cockroaches. The data of Tables I–IV also suggests that a borate compound used with a compound resulting in elevated concentrations of cAMP would be effective in controlling other pests, including insects and non-insects. For other pests, however, the concentrations of the toxins and synergists may vary from those set forth in the tables.

The foregoing description provides specific embodiments of the present invention. It should be appreciated that these embodiments are described for the purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

What is claimed is:

1. A synergistic pest-controlling composition comprising by percentage weight per total bait weight:

about 0.1%, to 6% of boric acid; and a compound resulting in elevated concentrations of 3'-5'-cyclic adenosine monophosphate (cAMP), said compound resulting in elevated concentration of cAMP being about 1% to 6% papaverine as a phosphodiesterase enzyme (PDE) inhibitor and an activator of cAMP production.

2. A pest-controlling composition according to claim 1, comprising about 0.1% boric acid, and about 1% papaverine.

3. A pest-controlling composition according to claim 1, comprising about 0.2% boric acid, and about 1% papaverine.

4. A pest-controlling composition according to claim 1, comprising about 0.4% boric acid, and about 1% papaverine.

5. A pest-controlling composition according to claim 1, comprising about 1% boric acid, and about 1% papaverine.

6. A pest-controlling composition according to claim 1, comprising about 3% boric acid, and about 1% papaverine.

7. A pest-controlling composition according to claim 1, comprising about 6% boric acid, and about 1% papaverine.

* * * * *